US006777242B1

(12) United States Patent
Gautier et al.

(10) Patent No.: US 6,777,242 B1
(45) Date of Patent: Aug. 17, 2004

(54) AQUEOUS SOLUTION BASED ON AN AZO DYE, PROCESS FOR ITS MANUFACTURE AND USE THEREOF

(75) Inventors: Jean-Pierre Gautier, Elancourt (FR); Frédérick Mantisi, Yerres (FR)

(73) Assignee: Atofina, Puteaux (FR)

( * ) Notice: Subject to any disclaimer, the term of this patent is extended or adjusted under 35 U.S.C. 154(b) by 0 days.

(21) Appl. No.: 09/394,647

(22) Filed: Sep. 8, 1999

(30) Foreign Application Priority Data

Sep. 9, 1998 (FR) .......................................... 98 11272

(51) Int. Cl.$^7$ .............................................. G01N 33/18
(52) U.S. Cl. ........................ 436/125; 436/124; 436/166
(58) Field of Search ................................ 436/124–125, 436/164, 166

(56) References Cited

U.S. PATENT DOCUMENTS

| | | | |
|---|---|---|---|
| 3,620,676 A | * | 11/1971 | Davis |
| 3,768,974 A | * | 10/1973 | Storm |
| 4,880,556 A | * | 11/1989 | Hutchings .................... 252/156 |
| 5,145,485 A | * | 9/1992 | Michna et al. .................. 8/527 |
| 5,155,048 A | | 10/1992 | Williams et al. |
| 5,362,650 A | | 11/1994 | Harp |
| 5,397,710 A | * | 3/1995 | Steinman ..................... 436/79 |

FOREIGN PATENT DOCUMENTS

| | | | |
|---|---|---|---|
| JP | 57-113350 | | 7/1982 |
| JP | 59-27249 | | 2/1984 |
| JP | 62-129744 | * | 6/1987 |

OTHER PUBLICATIONS

M. H. Hashmi et al, Anal. Chem. 1963, 35, 2194–2195.*
K. Ascik et al, Przegl. Papier 1974, 30, 466,472.*
H. Kanazawa et al, Sci. Rep. Fukushima Univ. 1991, 48, 37–47.*
B. Chiswell et al, Anal. Chim. Acta 1991, 249, 519–524.*
B. Chiswell et al, Analyst 1991, 116, 657–661.*
H. Kanazawa et al, Bull. Chem. Soc. Jpn. 1995, 68, 2483–2489.*
G. Gordon et al, Environ. Lab.: Moving 21st Century, Proc. 1997, 9/29–9/41.*
R. Hofmann et al, Environ Technol. 1998, 19, 761–773.*
J. R. Knechtel et al, Anal. Chem. 1978, 50, 202–205.*
R. Tinoco et al, Anal. Biochem. 1996, 241, 18–22.*
A. D. Sosimenko et al, J. Chromatog. 1991, 546, 37–59.*
D. P. Hautman et al, J. Chromatog. 1992, 602, 65–74.*
N. Imaizumi et al, Chemistry Letters 1993, 1333–1336.*
Y. Feng et al, Lihua Jianyan, Huaxue Fence 1999, 35, 268–269.*
M. Lepeintre et al, Chem. Abstr. 1961, 55, abstract 10191 g–h.*
P. Kerenyi et al, Chem. Abstr. 1963, 59, abstract 12507a.*
D. A. Hollowell et al, Anal. Chem. 1985, 57, 2851–2854.*
W. J. Masschelein et al, Ozone Sci. Eng. 1989, 11, 209–215.*
Serdyuk, L. S. et al, Chemical Abstracts 1964, 60, abstract 2325c.*
Galvez, J. et al, Electrochimica Acta 1982, 27, 1253–1257.*
Liptak, M. et al, Organic Mass Spectrometry 1993, 28, 780–784.*
W.Masschelein; "Spectrophotometric Determination of Chlorine Dioxide with Acid Chrome Violet K"; Analytical Chemistry vol. 38, No. 13; Dec. 1966 pp. 1839–1841.
I.J. Fletcher et al.; "Determination of Chlorine Dioxide in Portable Waters Using Chlorophenol Red"; Analyst; vol. 110, Jun. 1985; pp. 695–699.

* cited by examiner

Primary Examiner—Arlen Soderquist
(74) Attorney, Agent, or Firm—Thomas F. Roland

(57) ABSTRACT

The present invention relates to a stable aqueous solution (A) comprising an azo dye, a borate buffer and one or more masking agents, wherein the azo dye changes its coloration or coloration intensity in the presence of chlorine dioxide. The present invention further relates to a process for manufacturing the aqueous azo-dye solution (A), and to its use for the determination of residual chlorine dioxide in water.

19 Claims, No Drawings

AQUEOUS SOLUTION BASED ON AN AZO DYE, PROCESS FOR ITS MANUFACTURE AND USE THEREOF

1. BACKGROUND OF THE INVENTION

1.1 Technical Field

The present invention relates to a stable aqueous solution (A) comprising an azo dye, a borate buffer and one or more masking agents, wherein the azo dye changes its coloration or coloration intensity in the presence of chlorine dioxide. The present invention further relates to a process for manufacturing the stable aqueous azo-dye solution (A), and to its use for the determination of residual chlorine dioxide in water.

1.2 Background of Art

Since the discovery of the interactions between chlorine and the microorganisms present in untreated water and the resulting formation of toxic compounds, such as trihalomethanes, many studies have been carried out worldwide in order to find replacement solutions for disinfecting drinking water. Among the disinfectants proposed is chlorine dioxide. Accordingly, in recent decades, chlorine dioxide has been used in many countries to disinfect drinking waters and to condition industrial waters.

Since a certain amount of disinfectant must be present in the treated water to prevent it from being recontaminated, it is essential to determine accurately the residual amount of the disinfectant in the water.

Moreover, during the treatment of water and the period in the distribution network, chlorine dioxide participates in various oxidation reactions which lead to the formation of reduction/decomposition by-products, mainly consisting of chlorides, chlorates and chlorates. Thus, it is necessary to have a reliable method for determining the chlorine dioxide content in the treated water even in the presence of other oxidizing agents and chloro-compounds.

Lastly, the process for determining the chlorine dioxide content in water should comprise a limited number of operations and should be able to be carried out directly on site so as to avoid a loss of chlorine dioxide by degassing.

Although several methods have been proposed for determining chlorine dioxide, none of them satisfy all the above-mentioned criteria. Various methods, particularly colorimetric methods, available to date are listed in the thesis by J. D. Peak, Edmonton, Alberta, 1991. According to J. D. Peak, because of their virtually unselective natures, these colorimetric methods have been excluded from routine practices in industry.

Specifically, the method using DPD (N,N-diethyl-p-phenylenediamine sulphate), which is not sufficiently selective, often leads to erroneous results. Furthermore, it cannot determine the chlorine dioxide contents less than 0.1 mg/l.

Similarly, the method based on the decolorization of Alizarin Violet 3R (ACVK), developed by W. J. Masschelein (*Analytical Chemistry*, 38:1839, 1996) has a quantification threshold greater than 0.1 mg/l of chlorine dioxide.

To make the Chlorophenol Red (CPR) method selective, J. Fletcher and P. Hemmings (*Analyst*, 110:695, 1985) have proposed to use masking agents. This method, which involves several steps, consists of mixing the sample with a sodium cyclamate solution, adding immediately a buffer solution with stirring, followed by a chlorophenol red solution, and finally adding a thioacetamide solution. By measuring the absorbance of the final mixture at 520 nm using a UV-visible spectrophotometer, the residual content of chlorine dioxide in the sample can be determined.

However, the major drawback of this method is that it involves many steps of placing the sample in contact with a series of reagents and thus leads to a considerable and uncontrolled loss of chlorine dioxide by degassing (up to 30%).

2. SUMMARY OF THE INVENTION

The present invention by the applicants provides an aqueous solution (A) comprising an azo dye, a borate buffer and one or more masking agents, wherein the azo dye changes its coloration or coloration intensity in the presence of chlorine dioxide, and now makes it possible to determine accurately and selectively the residual content of chlorine dioxide in water, in particular, in drinking water.

The azo dye is advantageously chosen from amaranth (trisodium salt of 1-(4-sulfo-1-naphthylazo)-2-naphthol-3,6-disulfonic acid, $C_{20}H_{11}N_2Na_3O_{10}S_3$), C.I. 16185, and Evans blue (tetrasodium salt of 6,6'-[(3,3'-dimethyl[1,1'-biphenyl]-4,4'-diyl)bis(azo)]bis[4-amino-5-hydroxy-1,3-naphthalenedisulfonic acid, $C_{34}H_{24}N_6Na_4O_{14}S_4$], C.I. 23860.

The concentration of azo dye in solution (A) is generally between about $1 \times 10^{-6}$ and about $1 \times 10^{-3}$ M. It is preferably between about $2 \times 10^{-5}$ and about $8 \times 10^{-4}$ M. An amaranth concentration of about $2 \times 10^{-4}$ M has been found to be particularly advantageous. When the dye is Evans blue, a concentration of about $5 \times 10^{-5}$ M is advantageously chosen.

The borate ion is generally present in solution (A) in a proportion of from about $5 \times 10^{-3}$ to about $1 \times 10^{-1}$ M. A borate ion concentration of about $5 \times 10^{-2}$ M is preferred.

In this specification, the term "masking agent" means any compound capable of reacting with free chlorine: for example, glycine, cyclamate of alkali metal or alkaline earth metal, and aqueous ammonia. The amount of masking agent(s) used in solution (A) depends on its (their) nature. Preferably, aqueous ammonia is used, and in an amount advantageously between about 1 and about 4 g/l of solution (A).

The aqueous azo-dye solution according to the present invention can further comprise one or more metal-chelating agents such as EDTA (ethylenediaminetetra-acetic acid) salts. The amount of chelating agent(s) used varies depending on its (their) nature. In the case of the sodium salt of EDTA, the amount used per liter of solution (A) is generally between about 0.5 and about 2 g and preferably about 1 g. The solution (A) which is most particularly suitable contains, per liter, about $5 \times 10^{-2}$ mol of borate, about $1.5 \times 10^{-2}$ mol of aqueous ammonia, about 1 g of sodium salt of EDTA, and about $2 \times 10^{-4}$ mol of amaranth or about $5 \times 10^{-5}$ mol of Evans blue.

Another subject of the invention is a process for manufacturing a solution (A). In general, this process comprises following steps:

(a) a buffered aqueous azo-dye solution is prepared by introducing the azo dye, the masking agent(s) and the borate buffer solution into a container containing a sufficient amount of double-deionized water;

(b) the chelating agent dissolved in advance in double-deionized water is optionally added thereto, with stirring; and (c) the solution is made up to the desired volume with double-deionized water.

A pH of the aqueous azo-dye solution prepared in step (a), should be preferably about 9.2.

More particularly, the process for manufacturing a solution (A) comprises the following successive steps:

(i) the azo dye is dissolved in double-deionized water in a container;

(ii) a borate buffer solution is then introduced therein, followed by a solution of masking agent(s);

(iii) double-deionized water is added thereto and the pH is measured;

(iv) the pH is adjusted to about 9.2, if necessary;

(v) the chelating agent is optionally dissolved, with stirring; and (vi) the solution is made up to the desired volume with double-deionized water.

Advantageously, an aqueous ammonia solution is used to adjust the pH. A concentrated aqueous ammonia solution at about 28% by weight is particularly suitable to be used for pH adjustment and as a masking agent.

The aqueous azo-dye solution (A) thus prepared remains stable at room temperature for at least one month in a closed bottle.

Yet another subject of the present invention is a process for determining the residual chlorine dioxide content in an industrial water or drinking water after biocidal treatment or disinfection and in distribution circuits. This process consists of placing the water to be analyzed in contact with the aqueous solution (A) and then measuring the absorbance of the resultant solution (S) using a UV-visible spectrophotometer, at the specific wavelength for the azo dye chosen. This is 521 nm in the case of amaranth and 606 nm in the case of Evans blue.

This operation of placing two solutions in contact is generally carried out in the volume ratio: the water to be analyzed (water sample)/the aqueous solution (A), to be between about 10 and about 30 and preferably about 24.

As a reference for the absorbance measurement, the water sample itself to which a sufficient amount of a reducing agent is added, is used. As a reducing agent, an agent which particularly reduces chlorine dioxide, such as sodium thiosulphate, is preferable.

Advantageously, the water sample is placed in contact with solution (A) containing, per liter, about $5 \times 10^{-2}$ mol of borate, about $1.5 \times 10^{-2}$ mol of aqueous ammonia, about 1 g of sodium salt of EDTA and about $2 \times 10^{-4}$ mol of amaranth or about $5 \times 10^{-5}$ mol of Evans blue.

Preferably, the water sample is taken directly from the source and the operation of placing it in contact with the solution (A) is carried out by dipping the outlet of the water sample container directly into the solution (A). Working in this way makes it possible to avoid any loss of chlorine dioxide by degassing and to minimize errors arising from the sample transferring.

The absorbance of the resultant solution at the specific wavelength for the azo dye chosen is then measured in a quartz cuvette with an optical path length of 2.5 cm, using a UV-visible spectrophotometer and, as a reference, the water sample to which sodium thiosulphate has been added.

By plotting the absorbance measurement on a calibration curve relative to the reference, the residual chlorine dioxide content in the water sample is obtained. The calibration curve is generally pre-established by a common method based on known concentrations of chlorine dioxide solutions, and only the linear part of the calibration curve (i.e., less than 500 μg of $ClO_2$ per liter) is used.

The determination process can be readily adapted to spectrophotometers equipped with different optical path lengths (1, 5 or 10 cm) by adjusting the concentration of the dye in solution (A) and by establishing the corresponding calibration curve.

The process according to the present invention thus makes it possible to selectively determine the residual chlorine dioxide content in drinking water or industrial water, down to a concentration as low as 6 μg/l. Furthermore, after placing the aqueous solution (A) in contact with the water sample, the UV-visible spectrophotometric measurement can be made even 7 to 10 days later.

3. DESCRIPTION OF PREFERRED EMBODIMENTS

The following examples illustrate preferred embodiments of the present invention.

EXAMPLE 1

(1) Preparation of Solution (A).

One (1) liter of solution (A) is prepared as follows:

(i) dissolve 121.2 mg of amaranth [Ref. A-1016(97), Sigma] in about 100 ml of double-deionized water;

(ii) dissolve 3.09 g of boric acid in 500 ml of 0.1 M KCl solution and mix it to homogeneity;

(iii) add successively the solutions prepared in (i) and (ii) and 1 ml of 28% (w/w) aqueous ammonia solution into a one (1)-liter beaker;

(iv) add 300 ml of double-deionized water to the mixture of (iii);

(v) adjust the pH of the mixture to 9.2 using 28% (w/w) aqueous ammonia solution;

(vi) add 1 g of sodium salt of EDTA to the mixture of (v) and stir until EDTA is completely dissolved; and (vii) transfer the solution obtained from (vi) into a 1000-ml graduated flask and bring the volume up to the graduation mark with double-deionized water.

(2) Preparation of Chlorine Dioxide Standard Solutions

A stock solution of chlorine dioxide at a concentration of about 10 mg/l is prepared by diluting in double-deionized water a chlorine dioxide solution obtained as follows:

(i) decompose sodium chlorite in the presence of sulfuric acid;

(ii) purify the chlorine dioxide formed in (i) by bubbling into a chlorite solution; and (iii) dissolve the chlorine dioxide thus purified in double-deionized water.

The absorbance of the stock solution at 360 nm is then measured using a UV-visible spectrophotometer in a 5 cm quartz cuvette, after adjusting the machine to zero absorbance against the double-ionized water.

The concentration of the stock solution can be calculated using the formula:

$$C = \frac{AB \times 67450}{1250 \times L}$$

in which

C denotes the concentration of the stock solution (mg $ClO_2$/l);

AB denotes the absorbance of the solution; and

L denotes the path length of the cuvette, in cm.

The values 1250 and 67450 correspond to the molar absorption in $M^{-1}$ $cm^{-1}$ and the molecular weight, respectively, of chlorine dioxide.

(3) Calibration Curve of the Decolorization of Amaranth

Six (6) standard solutions with chlorine dioxide concentrations ranging from 20 to 500 μg/l are prepared by introducing 10 ml of solution (A) into each of six 250-ml graduated flasks, followed by different volumes (V), depending on a desired concentration, of the stock solution.

Each volume (V) of the stock solution is picked up using a precision pipette and introduced into the graduated flask containing solution (A) by immersing the tip of the pipette into the solution (A), without stirring or trickling down the wall of the flask, so as to avoid any loss of chlorine dioxide by degassing.

The standard solution thus prepared is then made up to the graduation mark with double-deionized water and mixed to homogeneity, taking care to avoid any loss of chlorine dioxide. Finally, the solution is left to stand for 30 seconds. The resultant solutions are stable for at least one week.

The reference (R) is prepared by introducing 10 ml of the solution (A) into the seventh graduated flask and making it up to the graduation mark with double-deionized water. The absorbance at 521 nm is measured for each standard solution relative to the reference, using a UV-visible spectrophotometer with 2.5 cm cuvettes. The calibration curve giving the absorbance measured as a function of the chlorine dioxide concentration of the standard solutions is then plotted.

(4) Determination of the Residual Chlorine Dioxide Content in the Treated Drinking Water Ten (10) ml of the aqueous solution obtained in (vii) of Example 1(1) are placed in a 250-ml graduated flask and the water sample, obtained in a tube directly from the source, to be analyzed was carefully added by dipping the tube directly into the solution (A). Taking care not to lose chlorine dioxide, the solution is mixed to homogeneity and thus prepared sample stays stable for 7 to 10 days.

The absorbance of the resultant solution at 521 nm is measured using a UV-visible spectrophotometer in a quartz cuvette with an optical path length of 2.5 cm. The reference is the same water sample to which purified and crystallized sodium thiosulphate has been added in excess of the amount required to reduce all the oxidizing agents present in the water sample.

The residual chlorine dioxide content in the water sample is then determined by plotting the absorbance measured on the calibration curve.

EXAMPLE 2

The same process as in Example 1 is performed, except that 56.5 mg of Evans blue (Ref. 20,633-4, Aldrich) is dissolved instead of 121.2 mg of amaranth. The absorbance of the standard solutions and that of the water sample are measured at 606 nm instead of 521 nm.

What is claimed is:

1. An aqueous solution comprising from about $1 \times 10^{-6}$ to about $1 \times 10^{-3}$ mol/liter of an azo dye selected from the group consisting of amaranth and Evans blue, a borate buffer and one or more masking agents, wherein the azo dye changes its coloration or coloration intensity in the presence of chlorine dioxide.

2. The aqueous solution according to claim 1, wherein the azo dye is present at a concentration of between about $2 \times 10^{-5}$ and about $8 \times 10^{-4}$ mol/liter.

3. The aqueous solution according to claim 1, wherein the masking agent is aqueous ammonia.

4. The aqueous solution according to claim 1, wherein the borate is present at a concentration of between about $5 \times 10^{-3}$ and about $1 \times 10^{-1}$ mol/liter.

5. The aqueous solution according to claim 1, further comprising one or more metal-chelating agents.

6. The aqueous solution according to claim 5, wherein the metal-chelating agent is a sodium salt of EDTA.

7. The aqueous solution according to claim 6, wherein the sodium salt of EDTA is present at a concentration of between about 0.5 and about 2 g/liter.

8. The aqueous solution according to claim 7, wherein aqueous solution contains about $5 \times 10^{-2}$ mol/l of borate, about $1.5 \times 10^{-2}$ mol/l of aqueous ammonia as the masking agent, about 1 g/l of sodium salt of EDTA and about $2 \times 10^{-4}$ mol/l of amaranth as the azo dye.

9. An aqueous solution comprising Evans blue azo dye present at a concentration of about $5 \times 10^{-5}$ mol/l, a borate buffer, aqueous ammonia present at a concentration of about $1.5 \times 10^{-2}$ mol/l, and a sodium salt of EDTA present at a concentration of about 1 g/l, wherein the aqueous solution contains about $5 \times 10^{-2}$ mol/l of borate and the azo dye changes its coloration or coloration intensity in the presence of chlorine dioxide.

10. A process for determining a residual chlorine dioxide content in industrial water or drinking water after treatment or in distribution circuits, comprising the steps of:

placing the water to be analyzed in contact with the aqueous solution of claim 8 or 9, wherein a volume ratio:

the water to be analyzed/the aqueous solution is between about 10 and about 30; and measuring an absorbance of the resultant solution using a UV-visible spectrophotometer at a specific wavelength of the azo dye chosen.

11. The process according to claim 10, wherein about 10 ml of the aqueous solution are placed into a 250 ml graduated flask and made up to the graduation mark with the water to be analyzed; and an absorbance of the resultant solution is measured using a UV-visible spectrophotometer at 521 nm for amaranth or at 606 nm for Evans blue.

12. The process according to claim 11, wherein an absorbance is measured using, as a reference, the water to be analyzed to which purified and crystallized sodium thiosulphate has been added in excess of the amount required to reduce any oxidizing agents present in the water.

13. A process for manufacturing the aqueous solution according to one of claims 1 and 2 through 9, comprising the steps of:

(a) introducing the azo dye, the masking agent(s) and the borate buffer solution into a container containing a sufficient amount of double-deionized water;

(b) optionally adding the chelating agent predissolved in double-deionized water with stirring; and (c) making up the solution to a desired volume with double-deionized water.

14. The process according to claim 13 further comprising the steps of:

(i) dissolving the azo dye in double-deionized water;

(ii) introducing into a container the solution prepared in (i), followed by a borate buffer solution, and finally a solution containing one or more masking agents;

(iii) adding double-deionized water and measuring pH;

(iv) adjusting pH to about 9.2, if necessary, using concentrated aqueous ammonia solution;

(v) optionally adding the chelating agent with stirring; and (vi) making up the solution to a desired volume with double-deionized water.

15. The process according to claim 14, wherein the concentrated aqueous ammonia solution at about 28% (w/w) is used in the step (ii) as a masking agent and in the step (iv).

16. The process according to claim 15 further comprising the steps of:
  (i) dissolving either about 121.2 mg of amaranth [Ref. A-1016(97) Sigma] or about 56.5 mg of Evans blue (Ref. 20,6334-4, Aldrich) in about 100 ml of double-deionized water;
  (ii) dissolving about 3.09 g of boric acid in 500 ml of 0.1 M KCl solution and mixing it to homogeneity to prepare about $5 \times 10^{-2}$ M borate buffer;
  (iii) successively introducing into a one-liter flask, the amaranth or Evans blue solution prepared in (i), the borate buffer solution prepared in (ii), and about 1 ml of about 28% (w/w) aqueous ammonia solution;
  (iv) adding double-deionized water and measuring pH;
  (v) adjusting pH to about 9.2 using about 285 (w/w) aqueous ammonia solution;
  (vi) adding about 1 g of sodium salt of EDTA with stirring until it completely dissolves; and
  (vii) transferring the solution prepared in (vi) into a 1000-ml graduated flask and making up the total volume to the graduation mark with double deionized water.

17. A process for determining a residual chlorine dioxide content in industrial water or drinking water after treatment or in distribution circuits, comprising the steps of:
  placing the water to be analyzed in contact with the aqueous solution prepared by the process according to claim 12; and
  measuring an absorbance of the resultant solution using a UV-visible spectrophotometer at a specific wavelength of the azo dye chosen.

18. The process according to claim 17, wherein a volume ratio:
  the water to be analyzed/the aqueous solution is between about 10 and about 30.

19. The aqueous solution according to claim 1, wherein the azo dye is amaranth.

* * * * *